(12) United States Patent
Sun et al.

(10) Patent No.: US 10,745,676 B2
(45) Date of Patent: Aug. 18, 2020

(54) POLYPEPTIDES HAVING PHOSPHOLIPASE C ACTIVITY AND POLYNUCLEOTIDES ENCODING SAME

(71) Applicant: Novozymes A/S, Bagsvaerd (DK)

(72) Inventors: Tianqi Sun, Beijing (CN); Ye Liu, Beijing (CN); Ming Li, Beijing (CN); Kim Borch, Birkeroed (DK)

(73) Assignee: Novozymes A/S, Bagsvaerd (DK)

( * ) Notice: Subject to any disclaimer, the term of this patent is extended or adjusted under 35 U.S.C. 154(b) by 30 days.

(21) Appl. No.: 16/152,043

(22) Filed: Oct. 4, 2018

(65) Prior Publication Data

US 2019/0024063 A1 Jan. 24, 2019

Related U.S. Application Data

(62) Division of application No. 14/649,084, filed as application No. PCT/CN2013/089106 on Dec. 11, 2013, now abandoned.

(60) Provisional application No. 61/756,745, filed on Jan. 25, 2013.

(30) Foreign Application Priority Data

Dec. 11, 2012 (WO) ................ PCT/CN2012/086378

(51) Int. Cl.
*C12N 15/82* (2006.01)
*C12N 9/16* (2006.01)
*C11B 3/00* (2006.01)
*C11B 3/04* (2006.01)
*A23D 9/013* (2006.01)

(52) U.S. Cl.
CPC ................ *C12N 9/16* (2013.01); *A23D 9/013* (2013.01); *C11B 3/003* (2013.01); *C11B 3/04* (2013.01); *C12N 15/8247* (2013.01); *C12Y 301/04003* (2013.01)

(58) Field of Classification Search
None
See application file for complete search history.

(56) References Cited

U.S. PATENT DOCUMENTS

| 7,993,874 B2 | 8/2011 | Nagasaki | |
| 2009/0053768 A1* | 2/2009 | Nagasaki | C12N 9/16 435/71.2 |
| 2011/0093965 A1* | 4/2011 | O'Donoghue | C12N 9/16 800/14 |

FOREIGN PATENT DOCUMENTS

| EP | 2368978 A1 | 9/2011 |
| WO | 2008/094847 A1 | 8/2008 |
| WO | 2012/062817 A1 | 5/2012 |

OTHER PUBLICATIONS

Apiyo et al., 2005, Biochemistry, vol. 44, No. 30, pp. 9980-9989.
Ciofalo et al, 2006, Regulatory toxicology and pharmacology, vol. 45, pp. 1-6.
Klein et al., 2011, Journal of Biological Chemistry, vol. 286, No. 14, pp. 12407-12416.
Li et al, 2004, China Oils and Fats, vol. 29, No. 1, pp. 19-22.
Titball., 1993, Microbiological Reviews, vol. 57, No. 2 pp. 347-366.

* cited by examiner

*Primary Examiner* — Elizabeth F McElwain
(74) *Attorney, Agent, or Firm* — Elias Lambiris

(57) ABSTRACT

The present invention relates to isolated polypeptides having phospholipase C activity, and polynucleotides encoding the polypeptides. The invention also relates to nucleic acid constructs, vectors, and host cells comprising the polynucleotides as well as methods of producing and using the polypeptides.

15 Claims, No Drawings
Specification includes a Sequence Listing.

SEQUENCE LISTING

```
<160> NUMBER OF SEQ ID NOS: 2

<210> SEQ ID NO 1
<211> LENGTH: 1833
<212> TYPE: DNA
<213> ORGANISM: Penicillium emersonii
<220> FEATURE:
<221> NAME/KEY: sig_peptide
<222> LOCATION: (1)..(48)
<220> FEATURE:
<221> NAME/KEY: CDS
<222> LOCATION: (1)..(1830)
<220> FEATURE:
<221> NAME/KEY: mat_peptide
<222> LOCATION: (49)..(1830)

<400> SEQUENCE: 1 atg aga gtt ctc gcc ctc atc gct gct ctg gcc acg gtg gcc acc gca      48
Met Arg Val Leu Ala Leu Ile Ala Ala Leu Ala Thr Val Ala Thr Ala
    -15                 -10                  -5                 -1 agt gcc ccc tat gac aag cgc gac ttg gcc cag gag att tgg gac gac      96
Ser Ala Pro Tyr Asp Lys Arg Asp Leu Ala Gln Glu Ile Trp Asp Asp
  1               5                  10                  15 atc aag aat gcg gtg gat tgc gct ggc tgc cag gtc gtt ctg act gcc     144
Ile Lys Asn Ala Val Asp Cys Ala Gly Cys Gln Val Val Leu Thr Ala
                 20                  25                  30 ctg aag ggt gtg gcc gat ctg ggc acg act gcc ctt gtc gat gtg ctg     192
Leu Lys Gly Val Ala Asp Leu Gly Thr Thr Ala Leu Val Asp Val Leu
             35                  40                  45 acc gaa gtg tgc aac atc agt ggc aaa gaa gat tcc gat gtc tgc tcg     240
Thr Glu Val Cys Asn Ile Ser Gly Lys Glu Asp Ser Asp Val Cys Ser
         50                  55                  60 ggc atc atc tcc cgc gag ggt ccg gtg ctg gat tat gtc ctg cag cac     288
Gly Ile Ile Ser Arg Glu Gly Pro Val Leu Asp Tyr Val Leu Gln His
 65                  70                  75                  80 ctc gat atc ggc tcg cac acc tcc cag gtc atc tgt gcc agc gca ttc     336
Leu Asp Ile Gly Ser His Thr Ser Gln Val Ile Cys Ala Ser Ala Phe
                 85                  90                  95 ggc ctc tgc cag tat cct gag gtc cgg ccc tac aac ctc acc ttc cct     384
Gly Leu Cys Gln Tyr Pro Glu Val Arg Pro Tyr Asn Leu Thr Phe Pro
            100                 105                 110 aaa ccc aag ccc aac acg act cgt cca gaa ccc agt gga gag tca cca     432
Lys Pro Lys Pro Asn Thr Thr Arg Pro Glu Pro Ser Gly Glu Ser Pro
        115                 120                 125 atc cag gtc gtc cac ttc agc gat act cac gtg gac ctc tcc tac gag     480
Ile Gln Val Val His Phe Ser Asp Thr His Val Asp Leu Ser Tyr Glu
    130                 135                 140
```

-continued

| | | |
|---|---|---|
| acg ggg tcc aat tac aac tgt aca aag ccc atc tgc tgt cgc cct tac<br>Thr Gly Ser Asn Tyr Asn Cys Thr Lys Pro Ile Cys Cys Arg Pro Tyr<br>145                                150                       155                   160 | 528 |
| acg gcc gag gat gca ccg gga aac acg acg act ccg tgc ggg cca tat<br>Thr Ala Glu Asp Ala Pro Gly Asn Thr Thr Thr Pro Cys Gly Pro Tyr<br>                       165                      170                     175 | 576 |
| ggc aac acc aaa tgt gat gct ccc ttg agc ctc gag gag agc atg ttc<br>Gly Asn Thr Lys Cys Asp Ala Pro Leu Ser Leu Glu Glu Ser Met Phe<br>                 180                      185                     190 | 624 |
| gcc gcg atc aaa gcg ctc aac ccc cag ccc gcc ttt tcc att tat acg<br>Ala Ala Ile Lys Ala Leu Asn Pro Gln Pro Ala Phe Ser Ile Tyr Thr<br>195                       200                     205 | 672 |
| ggc gac gtc gtc gca cac gac atc tgg ctg gtg gat caa aac gag gtc<br>Gly Asp Val Val Ala His Asp Ile Trp Leu Val Asp Gln Asn Glu Val<br>210                       215                     220 | 720 |
| att gag gac ctg aat gcc acc tac gac cgc atg gcc ggg ctg ggg ctg<br>Ile Glu Asp Leu Asn Ala Thr Tyr Asp Arg Met Ala Gly Leu Gly Leu<br>225                       230                     235                   240 | 768 |
| gtc tat gcg gcc att ggg aat cac gac acg gcg ccg gtc aac gat ctg<br>Val Tyr Ala Ala Ile Gly Asn His Asp Thr Ala Pro Val Asn Asp Leu<br>                 245                      250                     255 | 816 |
| ccg acg agc aac atc ccc agc gag tac agc gcg aac tgg acc tac gag<br>Pro Thr Ser Asn Ile Pro Ser Glu Tyr Ser Ala Asn Trp Thr Tyr Glu<br>                 260                      265                     270 | 864 |
| gcc ctc tcg tac gac ttt acg atg ctg acg cag tcg gcc tct gcc cag<br>Ala Leu Ser Tyr Asp Phe Thr Met Leu Thr Gln Ser Ala Ser Ala Gln<br>                 275                      280                     285 | 912 |
| acc gcg gcg aat tac ggg tct tat tcg gcc atc tat ccc ggc agc tac<br>Thr Ala Ala Asn Tyr Gly Ser Tyr Ser Ala Ile Tyr Pro Gly Ser Tyr<br>290                       295                     300 | 960 |
| ggc acg gat ctc cgc gtc att tcc tac aac agc atc ttc tac tac gtg<br>Gly Thr Asp Leu Arg Val Ile Ser Tyr Asn Ser Ile Phe Tyr Tyr Val<br>305                       310                     315                   320 | 1008 |
| gac aat ttc tgg gcg tac caa gat cct atg gaa ttc gac ccg gat gga<br>Asp Asn Phe Trp Ala Tyr Gln Asp Pro Met Glu Phe Asp Pro Asp Gly<br>                       325                      330                     335 | 1056 |
| caa ctg gcc tgg ctg atc aac gag ctc cag gag gcc gag acg gcg ggg<br>Gln Leu Ala Trp Leu Ile Asn Glu Leu Gln Glu Ala Glu Thr Ala Gly<br>                 340                      345                     350 | 1104 |
| cag cgg gtc tgg att att gcg cat gtg ccg acg ggc acg tcg gat cac<br>Gln Arg Val Trp Ile Ile Ala His Val Pro Thr Gly Thr Ser Asp His<br>                 355                      360                     365 | 1152 |
| ttc cac gac tat tcg cac tac ttt gac cag atc gtg cag cgc tac gag<br>Phe His Asp Tyr Ser His Tyr Phe Asp Gln Ile Val Gln Arg Tyr Glu<br>370                       375                     380 | 1200 |
| gcc act att gcg gcg ctg ttc tac ggc cac act cac atc gac cag ttc<br>Ala Thr Ile Ala Ala Leu Phe Tyr Gly His Thr His Ile Asp Gln Phe<br>385                       390                     395                   400 | 1248 |
| caa atc tcg tac tcg aac tat tcc aac cga gca ttc gac acg gcg acc<br>Gln Ile Ser Tyr Ser Asn Tyr Ser Asn Arg Ala Phe Asp Thr Ala Thr<br>                       405                      410                     415 | 1296 |
| gcc atc ggg tat atc atg ccg tca ttg act ccg acc tcg gga cct cct<br>Ala Ile Gly Tyr Ile Met Pro Ser Leu Thr Pro Thr Ser Gly Pro Pro<br>                 420                      425                     430 | 1344 |
| acc ttc cgg gtc tat gac gtt gat ccc aag acg ttt gcc gtg ctg gac<br>Thr Phe Arg Val Tyr Asp Val Asp Pro Lys Thr Phe Ala Val Leu Asp<br>                 435                      440                     445 | 1392 |
| ttc acc aac tac att gcc aac atc agc gac ccg gcg ttc cag tcg ggc<br>Phe Thr Asn Tyr Ile Ala Asn Ile Ser Asp Pro Ala Phe Gln Ser Gly<br>450                       455                     460 | 1440 |

```
ccg tcg tgg cag aag tac tac tcg gcc aag gag acg tac ggc tcg ttg    1488
Pro Ser Trp Gln Lys Tyr Tyr Ser Ala Lys Glu Thr Tyr Gly Ser Leu
465                 470                 475                 480 ctg tct cct cca gtg acg gac ccg acg gcg gag ctg acg ccg gcc ttc    1536
Leu Ser Pro Pro Val Thr Asp Pro Thr Ala Glu Leu Thr Pro Ala Phe
                485                 490                 495 tgg cac aac gtc acg gtg gcc ttt gag cag gac aac gcg acc ttc cag    1584
Trp His Asn Val Thr Val Ala Phe Glu Gln Asp Asn Ala Thr Phe Gln
            500                 505                 510 gag tac tgg gcg cgg cag acg cgg ggg tac gac gtg tcg agc tgc acg    1632
Glu Tyr Trp Ala Arg Gln Thr Arg Gly Tyr Asp Val Ser Ser Cys Thr
        515                 520                 525 ggg tcc tgc atc act cag gcc atc tgc ggc ctg cgc gcg gga gac gcg    1680
Gly Ser Cys Ile Thr Gln Ala Ile Cys Gly Leu Arg Ala Gly Asp Ala
    530                 535                 540 cag tac aac tgc gtg acg ccg acg ccg ggc ttc aac ttt gcc aaa cgg    1728
Gln Tyr Asn Cys Val Thr Pro Thr Pro Gly Phe Asn Phe Ala Lys Arg
545                 550                 555                 560 gat acc tcc aac ccc aag cag gct cta tct cat gtc gag aaa tgc gag    1776
Asp Thr Ser Asn Pro Lys Gln Ala Leu Ser His Val Glu Lys Cys Glu
                565                 570                 575 ggc tcg gga ttg ctg ggg ctg ctg cgc agg atg gtg gct gac agt aag    1824
Gly Ser Gly Leu Leu Gly Leu Leu Arg Arg Met Val Ala Asp Ser Lys
            580                 585                 590 tct tcc tag                                                        1833
Ser Ser

<210> SEQ ID NO 2
<211> LENGTH: 610
<212> TYPE: PRT
<213> ORGANISM: Penicillium emersonii

<400> SEQUENCE: 2

Met Arg Val Leu Ala Leu Ile Ala Ala Leu Ala Thr Val Ala Thr Ala
    -15                 -10                 -5                  -1

Ser Ala Pro Tyr Asp Lys Arg Asp Leu Ala Gln Glu Ile Trp Asp Asp
1               5                   10                  15

Ile Lys Asn Ala Val Asp Cys Ala Gly Cys Gln Val Val Leu Thr Ala
            20                  25                  30

Leu Lys Gly Val Ala Asp Leu Gly Thr Thr Ala Leu Val Asp Val Leu
        35                  40                  45

Thr Glu Val Cys Asn Ile Ser Gly Lys Glu Asp Ser Asp Val Cys Ser
    50                  55                  60

Gly Ile Ile Ser Arg Glu Gly Pro Val Leu Asp Tyr Val Leu Gln His
65                  70                  75                  80

Leu Asp Ile Gly Ser His Thr Ser Gln Val Ile Cys Ala Ser Ala Phe
                85                  90                  95

Gly Leu Cys Gln Tyr Pro Glu Val Arg Pro Tyr Asn Leu Thr Phe Pro
            100                 105                 110

Lys Pro Lys Pro Asn Thr Thr Arg Pro Glu Pro Ser Gly Glu Ser Pro
        115                 120                 125

Ile Gln Val Val His Phe Ser Asp Thr His Val Asp Leu Ser Tyr Glu
    130                 135                 140

Thr Gly Ser Asn Tyr Asn Cys Thr Lys Pro Ile Cys Cys Arg Pro Tyr
145                 150                 155                 160

Thr Ala Glu Asp Ala Pro Gly Asn Thr Thr Pro Cys Gly Pro Tyr
                165                 170                 175
```

-continued

Gly Asn Thr Lys Cys Asp Ala Pro Leu Ser Leu Glu Glu Ser Met Phe
            180                 185                 190

Ala Ala Ile Lys Ala Leu Asn Pro Gln Pro Ala Phe Ser Ile Tyr Thr
        195                 200                 205

Gly Asp Val Val Ala His Asp Ile Trp Leu Val Asp Gln Asn Glu Val
        210                 215                 220

Ile Glu Asp Leu Asn Ala Thr Tyr Asp Arg Met Ala Gly Leu Gly Leu
225                 230                 235                 240

Val Tyr Ala Ala Ile Gly Asn His Asp Thr Ala Pro Val Asn Asp Leu
                245                 250                 255

Pro Thr Ser Asn Ile Pro Ser Glu Tyr Ser Ala Asn Trp Thr Tyr Glu
            260                 265                 270

Ala Leu Ser Tyr Asp Phe Thr Met Leu Thr Gln Ser Ala Ser Ala Gln
        275                 280                 285

Thr Ala Ala Asn Tyr Gly Ser Tyr Ser Ala Ile Tyr Pro Gly Ser Tyr
        290                 295                 300

Gly Thr Asp Leu Arg Val Ile Ser Tyr Asn Ser Ile Phe Tyr Tyr Val
305                 310                 315                 320

Asp Asn Phe Trp Ala Tyr Gln Asp Pro Met Glu Phe Asp Pro Asp Gly
                325                 330                 335

Gln Leu Ala Trp Leu Ile Asn Glu Leu Gln Glu Ala Glu Thr Ala Gly
            340                 345                 350

Gln Arg Val Trp Ile Ile Ala His Val Pro Thr Gly Thr Ser Asp His
        355                 360                 365

Phe His Asp Tyr Ser His Tyr Phe Asp Gln Ile Val Gln Arg Tyr Glu
        370                 375                 380

Ala Thr Ile Ala Ala Leu Phe Tyr Gly His Thr His Ile Asp Gln Phe
385                 390                 395                 400

Gln Ile Ser Tyr Ser Asn Tyr Ser Asn Arg Ala Phe Asp Thr Ala Thr
                405                 410                 415

Ala Ile Gly Tyr Ile Met Pro Ser Leu Thr Pro Thr Ser Gly Pro Pro
            420                 425                 430

Thr Phe Arg Val Tyr Asp Val Asp Pro Lys Thr Phe Ala Val Leu Asp
        435                 440                 445

Phe Thr Asn Tyr Ile Ala Asn Ile Ser Asp Pro Ala Phe Gln Ser Gly
        450                 455                 460

Pro Ser Trp Gln Lys Tyr Tyr Ser Ala Lys Glu Thr Tyr Gly Ser Leu
465                 470                 475                 480

Leu Ser Pro Pro Val Thr Asp Pro Thr Ala Glu Leu Thr Pro Ala Phe
                485                 490                 495

Trp His Asn Val Thr Val Ala Phe Glu Gln Asp Asn Ala Thr Phe Gln
            500                 505                 510

Glu Tyr Trp Ala Arg Gln Thr Arg Gly Tyr Asp Val Ser Ser Cys Thr
        515                 520                 525

Gly Ser Cys Ile Thr Gln Ala Ile Cys Gly Leu Arg Ala Gly Asp Ala
        530                 535                 540

Gln Tyr Asn Cys Val Thr Pro Thr Pro Gly Phe Asn Phe Ala Lys Arg
545                 550                 555                 560

Asp Thr Ser Asn Pro Lys Gln Ala Leu Ser His Val Glu Lys Cys Glu
                565                 570                 575

```
Gly Ser Gly Leu Leu Gly Leu Leu Arg Arg Met Val Ala Asp Ser Lys
            580                 585                 590
Ser Ser
```

POLYPEPTIDES HAVING PHOSPHOLIPASE C ACTIVITY AND POLYNUCLEOTIDES ENCODING SAME

CROSS-REFERENCE TO RELATED APPLICATIONS

This application is a divisional of U.S. application Ser. No. 14/649,084 filed on Jun. 2, 2015, now abandoned, which is a 35 U.S.C. 371 national application of international application no. PCT/CN2013/089106 filed Dec. 11, 2013, which claims priority or the benefit under 35 U.S.C. 119 of International application no. PCT/CN2012/086378 filed Dec. 11, 2012 and U.S. provisional application No. 61/756,745 filed Jan. 25, 2013, the contents of which are fully incorporated herein by reference.

REFERENCE TO A SEQUENCE LISTING

This application contains a Sequence Listing in computer readable form, which is incorporated herein by reference.

BACKGROUND OF THE INVENTION

Field of the Invention

The present invention relates to polypeptides having phospholipase C activity and polynucleotides encoding the polypeptides. The invention also relates to nucleic acid constructs, vectors, and host cells comprising the polynucleotides as well as methods of producing and using the polypeptides.

Further, the present invention relates to a method for reducing the content of phosphorous containing components in edible oil comprising a high amount of non-hydratable phosphorus, by the use of the enzyme having phospholipase C activity.

Description of the Related Art

Several types of phospholipases are known which differ in their specificity according to the position of the bond attacked in the phospholipid molecule. Phospholipase A1 (PLA1) removes the 1-position fatty acid to produce free fatty acid and 1-lyso-2-acylphospholipid. Phospholipase A2 (PLA2) removes the 2-position fatty acid to produce free fatty acid and 1-acyl-2-lysophospholipid. The term phospholipase B (PLB) is used for phospholipases having both A1 and A2 activity. Phospholipase C (PLC) removes the phosphate moiety to produce 1,2 diacylglycerol and phosphate ester. Phospholipase D (PLD) produces 1,2-diacylglycero-phosphate and base group.

Polypeptides having phospholipase C activity may be applied in an industrial process, e.g., for refining of vegetable oils. Before consumption vegetable oils are degummed to provide refined storage stable vegetable oils of neutral taste and light color. The degumming process comprises removing the phospholipid components (the gum) from the triglyceride rich oil fraction.

Traditionally, the degumming process has been based on either water extraction, acidic or caustic treatment followed by a separation process. Due to the emulsifying properties of the phospholipid components, the degumming procedure has resulted in a loss of oil i.e. of triglycerides. Enzymatic degumming reduces the oils loss due to an efficient hydrolysis of the phospholipids which decrease the emulsifying properties. There is a need for further enzymes having phospholipase C activity and suitable for application in enzymatic degumming of edible oils.

An enzyme having phospholipase C activity and 88% sequence identity with the enzyme of the present invention is known from WO2012062817.

SUMMARY OF THE INVENTION

The inventors have isolated a new enzyme having phospholipase C activity from a strain of *Penicillium*, or more specifically from a strain of *Penicillium emersonii* found 2007 in China. Accordingly, the present invention provides novel polypeptides having phospholipase C activity and polynucleotides encoding the polypeptides.

The present invention relates to isolated polypeptides having phospholipase C activity selected from the group consisting of:

(a) a polypeptide having at least 90% sequence identity to the mature polypeptide of SEQ ID NO: 2;

(b) a polypeptide encoded by a polynucleotide that hybridizes under very high stringency conditions with (i) the mature polypeptide coding sequence of SEQ ID NO: 1, or (ii) the full-length complement of (i);

(c) a polypeptide encoded by a polynucleotide having at least 90% sequence identity to the mature polypeptide coding sequence of SEQ ID NO: 1;

(d) a variant of the mature polypeptide of SEQ ID NO: 2 comprising a substitution, deletion, and/or insertion at one or more (e.g., several) positions; and (e) a fragment of the polypeptide of (a), (b), (c), or (d) that has phospholipase C activity.

The present invention also relates to isolated polynucleotides encoding the polypeptides of the present invention; nucleic acid constructs; recombinant expression vectors; recombinant host cells comprising the polynucleotides; and methods of producing the polypeptides.

The present invention also relates to a composition comprising the polypeptides of the present invention The present invention also relates to use of the aforementioned polypeptide or the aforementioned composition in a process for hydrolysis of phospholipids, such as in a process to reduce the phospholipid content in an edible oil.

The present invention also relates to a transgenic plant, plant part or plant cell transformed with a polynucleotide encoding the polypeptides of the present invention.

Definitions

Phospholipase C activity: The term "phospholipase C activity" means the activity that catalyzes the reaction: A phosphatidylcholine+$H_2O$=1,2-sn-diacylglycerol+choline phosphate. Phospholipase C activity may be determined according to the procedure described in "Materials and Methods". An enzyme having "phospholipase C activity" may belong to EC 3.1.4.3.

The polypeptides of the present invention have at least 20%, e.g., at least 40%, at least 50%, at least 60%, at least 70%, at least 80%, at least 90%, at least 95%, and at least 100% of the phospholipase C activity of the mature polypeptide of SEQ ID NO: 2.

The term "phospholipase C activity" means that a polypeptide having phospholipase C will have activity towards one or more of phosphatidylcholine (PC), phosphatidylethanolamine (PE), phosphatidic acid (PA) and phosphatidyl inositol (PI).

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Catalytic domain: The term "catalytic domain" means the region of an enzyme containing the catalytic machinery of the enzyme.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Fragment: The term "fragment" means a polypeptide having one or more (e.g., several) amino acids absent from the amino and/or carboxyl terminus of a mature polypeptide; wherein the fragment has phospholipase C activity. In one aspect, a fragment contains at least 1700 amino acid residues (e.g., amino acids 1 to 1700 of SEQ ID NO: 2), at least 1600 amino acid residues (e.g., amino acids 1 to 1600 of SEQ ID NO: 2), or at least 1500 amino acid residues (e.g., amino acids 1 to 1500 of SEQ ID NO: 2).

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance). An isolated substance may be present in a fermentation broth sample.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 1 to 594 of SEQ ID NO: 2. Amino acids −16 to −1 of SEQ ID NO: 2 are a signal peptide. It is known in the art that a host cell may produce a mixture of two of more different mature polypeptides (i.e., with a different C-terminal and/or N-terminal amino acid) expressed by the same polynucleotide.

Mature polypeptide coding sequence: The term "mature polypeptide coding sequence" means a polynucleotide that encodes a mature polypeptide having phospholipase C activity. In one aspect, the mature polypeptide coding sequence is nucleotides 49 to 1830 of SEQ ID NO: 1. Nucleotides 1 to 48 of SEQ ID NO: 1 encode a signal peptide.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

$$(\text{Identical Residues} \times 100)/(\text{Length of Alignment} - \text{Total Number of Gaps in Alignment})$$

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of Alignment−Total Number of Gaps in Alignment)

Stringency conditions:

Very low stringency conditions: The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 45° C.

Low stringency conditions: The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

Medium stringency conditions: The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

Medium-high stringency conditions: The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and either 35% formamide, following standard Southern blotting procedures for 12 to 24 hours. The carrier material is finally washed three times each for 15 minutes using 2×SSC, 0.2% SDS at 60° C.

High stringency conditions: The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

Very high stringency conditions: The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

Subsequence: The term "subsequence" means a polynucleotide having one or more (e.g., several) nucleotides absent from the 5' and/or 3' end of a mature polypeptide coding sequence; wherein the subsequence encodes a fragment having phospholipase C activity. In one aspect, a subsequence contains at least 1800 nucleotides (e.g., nucleotides 1 to 1800 of SEQ ID NO: 1), at least 1700 nucleotides (e.g., nucleotides 1 to 1700 of SEQ ID NO: 1), or at least 1600 nucleotides (e.g., nucleotides 1 to 1600 of SEQ ID NO: 1).

Variant: The term "variant" means a polypeptide having phospholipase C activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position.

DETAILED DESCRIPTION OF THE INVENTION

Polypeptides Having Phospholipase C Activity

In an embodiment, the present invention relates to isolated polypeptides having a sequence identity to the mature polypeptide of SEQ ID NO: 2 of at least 90%, at least 91%, at least 92%, at least 93%, at least 94%, at least 95%, at least 96%, at least 97%, at least 98%, at least 99%, or 100%, which have phospholipase C activity. In one aspect, the polypeptides differ by no more than 10 amino acids, e.g., 1, 2, 3, 4, 5, 6, 7, 8, or 9, from the mature polypeptide of SEQ ID NO: 2.

A polypeptide of the present invention preferably comprises or consists of the amino acid sequence of SEQ ID NO: 2 or an allelic variant thereof; or is a fragment thereof having phospholipase C activity. In another aspect, the polypeptide comprises or consists of the mature polypeptide of SEQ ID NO: 2. In another aspect, the polypeptide comprises or consists of amino acids 1 to 594 of SEQ ID NO: 2.

In another embodiment, the present invention relates to an isolated polypeptide having phospholipase C activity encoded by a polynucleotide that hybridizes under very low stringency conditions, low stringency conditions, medium stringency conditions, medium-high stringency conditions, high stringency conditions, or very high stringency conditions with (i) the mature polypeptide coding sequence of SEQ ID NO: 1, or (ii) the full-length complement of (i) (Sambrook et al., 1989, *Molecular Cloning, A Laboratory Manual*, 2d edition, Cold Spring Harbor, New York).

The polynucleotide of SEQ ID NO: 1 or a subsequence thereof, as well as the polypeptide of SEQ ID NO: 2 or a fragment thereof, may be used to design nucleic acid probes to identify and clone DNA encoding polypeptides having phospholipase C activity from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may be screened for DNA that hybridizes with the probes described above and encodes a polypeptide having phospholipase C activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 1 or a subsequence thereof, the carrier material is used in a Southern blot.

For purposes of the present invention, hybridization indicates that the polynucleotide hybridizes to a labeled nucleic acid probe corresponding to (i) SEQ ID NO: 1; (ii) the mature polypeptide coding sequence of SEQ ID NO: 1; (iii) the full-length complement thereof; or (iv) a subsequence thereof; under very low to very high stringency conditions. Molecules to which the nucleic acid probe hybridizes under these conditions can be detected using, for example, X-ray film or any other detection means known in the art.

In one aspect, the nucleic acid probe is nucleotides 55 to 1900 nucleotides 100 to 1800, nucleotides 300 to 1200, or nucleotides 500 to 1000 of SEQ ID NO: 1. In another aspect, the nucleic acid probe is a polynucleotide that encodes the polypeptide of SEQ ID NO: 2; the mature polypeptide thereof; or a fragment thereof. In another aspect, the nucleic acid probe is SEQ ID NO: 1. In another embodiment, the present invention relates to an isolated polypeptide having phospholipase C activity encoded by a polynucleotide having a sequence identity to the mature polypeptide coding sequence of SEQ ID NO: 1 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to variants of the mature polypeptide of SEQ ID NO: 2 comprising a substitution, deletion, and/or insertion at one or more (e.g., several) positions. In an embodiment, the number of amino acid substitutions, deletions and/or insertions introduced into the mature polypeptide of SEQ ID NO: 2 is not more than 10, e.g., 1, 2, 3, 4, 5, 6, 7, 8 or 9. The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a polyhistidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for phospholipase C activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

Sources of Polypeptides Having Phospholipase C Activity

A polypeptide having phospholipase C activity of the present invention may be obtained from microorganisms of any genus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

The polypeptide may be a fungal polypeptide. For example, the polypeptide may be a yeast polypeptide such as a *Candida, Kluyveromyces, Pichia, Saccharomyces, Schizosaccharomyces*, or *Yarrowia* polypeptide; or a filamentous fungal polypeptide such as an *Acremonium, Agaricus, Alternaria, Aspergillus, Aureobasidium, Botryosphaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Kinochaeta, Lentinula, Leptospaeria, Magnaporthe, Melanocarpus, Meripilus, Metarhizium, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor,*

*Schizophyllum, Scytalidium, Talaromyces, Thermoascus, Thielavia, Tolypocladium, Trichoderma, Trichophaea, Verticillium, Volvariella,* or *Xylaria* polypeptide.

In another aspect, the polypeptide is a *Saccharomyces carlsbergensis, Saccharomyces cerevisiae, Saccharomyces diastaticus, Saccharomyces douglasii, Saccharomyces kluyveri, Saccharomyces norbensis,* or *Saccharomyces oviformis* polypeptide.

In another aspect, the polypeptide is an *Acremonium cellulolyticus, Aspergillus aculeatus, Aspergillus awamori, Aspergillus foetidus, Aspergillus fumigatus, Aspergillus japonicus, Aspergillus nidulans, Aspergillus niger, Aspergillus oryzae, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Kinochaeta sp., Mucor miehei, Myceliophthora thermophila, Neurospora crassa, Metarhizium anisopliae, Penicillium emersonii, Aspergillus fumigates, Penicillium funiculosum, Penicillium oxalicum, Penicillium purpurogenum, Penicillium Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia setosa, Thielavia spededonium, Thielavia subthermophila, Thielavia terrestris, Trichoderma harzianum, Trichoderma koningii, Trichoderma longibrachiatum, Trichoderma reesei,* or *Trichoderma viride* polypeptide.

In a preferred aspect, the polypeptide is a *Penicillium emersonii* polypeptide.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are known to those of ordinary skill in the art (see, e.g., Sambrook et al., 1989, supra).

Polynucleotides

The present invention also relates to isolated polynucleotides encoding a polypeptide of the present invention, as described herein.

The techniques used to isolate or clone a polynucleotide are known in the art and include isolation from genomic DNA or cDNA, or a combination thereof. The cloning of the polynucleotides from genomic DNA can be effected, e.g., by using the well-known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligation activated transcription (LAT) and polynucleotide-based amplification (NASBA) may be used. The polynucleotides may be cloned from a strain of *Penicillium*, or a related organism and thus, for example, may be an allelic or species variant of the polypeptide encoding region of the polynucleotide.

Modification of a polynucleotide encoding a polypeptide of the present invention may be necessary for synthesizing polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variants may be constructed on the basis of the polynucleotide presented as the mature polypeptide coding sequence of SEQ ID NO: 1, e.g., a subsequence thereof, and/or by introduction of nucleotide substitutions that do not result in a change in the amino acid sequence of the polypeptide, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95-107.

Nucleic Acid Constructs

The present invention also relates to nucleic acid constructs comprising a polynucleotide of the present invention operably linked to one or more control sequences that direct the expression of the coding sequence in a suitable host cell under conditions compatible with the control sequences.

A polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearother-* mophilus maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Dania (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, Microbiological Reviews 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory systems are those that cause expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked with the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram-positive or Gram-negative bacterium. Gram-positive bacteria include, but are not limited to, *Bacillus*, *Clostridium*, *Enterococcus*, *Geobacillus*, *Lactobacillus*, *Lactococcus*, *Oceanobacillus*, *Staphylococcus*, *Streptococcus*, and *Streptomyces*. Gram-negative bacteria include, but are not limited to, *Campylobacter*, *E. coli*, *Flavobacterium*, *Fusobacterium*, *Helicobacter*, *Ilyobacter*, *Neisseria*, *Pseudomonas*, *Salmonella*, and *Ureaplasma*.

The bacterial host cell may be any *Bacillus* cell including, but not limited to, *Bacillus alkalophilus*, *Bacillus amyloliquefaciens*, *Bacillus brevis*, *Bacillus circulans*, *Bacillus clausii*, *Bacillus coagulans*, *Bacillus firmus*, *Bacillus lautus*, *Bacillus lentus*, *Bacillus licheniformis*, *Bacillus megaterium*, *Bacillus pumilus*, *Bacillus stearothermophilus*, *Bacillus subtilis*, and *Bacillus thuringiensis* cells.

The bacterial host cell may also be any *Streptococcus* cell including, but not limited to, *Streptococcus equisimilis*, *Streptococcus pyogenes*, *Streptococcus uberis*, and *Streptococcus equi* subsp. *Zooepidemicus* cells.

The bacterial host cell may also be any *Streptomyces* cell including, but not limited to, *Streptomyces achromogenes*, *Streptomyces avermitilis*, *Streptomyces coelicolor*, *Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol.* (Praha) 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397) or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804), or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, Passmore, and Davenport, editors, Soc. App. Bacteriol. Symposium Series No. 9, 1980).

The yeast host cell may be a *Candida*, *Hansenula*, *Kluyveromyces*, *Pichia*, *Saccharomyces*, *Schizosaccharomyces*, or *Yarrowia* cell, such as a *Kluyveromyces lactis*, *Saccharomyces carlsbergensis*, *Saccharomyces cerevisiae*,

*Saccharomyces diastaticus, Saccharomyces douglasii, Saccharomyces kluyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phiebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a polypeptide of the present invention, comprising (a) cultivating a cell, which in its wild-type form produces the polypeptide, under conditions conducive for production of the polypeptide; and (b) recovering the polypeptide. In a preferred aspect, the cell is a *Penicillium* cell. In a more preferred aspect, the cell is a *Penicillium emersonii* cell.

The present invention also relates to methods of producing a polypeptide of the present invention, comprising (a) cultivating a recombinant host cell of the present invention under conditions conducive for production of the polypeptide; and (b) recovering the polypeptide.

The host cells are cultivated in a nutrient medium suitable for production of the polypeptide using methods known in the art. For example, the cell may be cultivated by shake flask cultivation, or small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure polypeptides.

In an alternative aspect, the polypeptide is not recovered, but rather a host cell of the present invention expressing the polypeptide is used as a source of the polypeptide.

Plants

The present invention also relates to isolated plants, e.g., a transgenic plant, plant part, or plant cell, comprising a polynucleotide of the present invention so as to express and produce a polypeptide in recoverable quantities. The polypeptide may be recovered from the plant or plant part. Alternatively, the plant or plant part containing the polypeptide may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, Poa), forage grass such as *Festuca, Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilization of the invention are also considered plant parts, e.g., embryos, endosperms, aleurone and seed coats.

Also included within the scope of the present invention are the progeny of such plants, plant parts, and plant cells.

The transgenic plant or plant cell expressing the polypeptide may be constructed in accordance with methods known in the art. In short, the plant or plant cell is constructed by incorporating one or more expression constructs encoding the polypeptide into the plant host genome or chloroplast genome and propagating the resulting modified plant or plant cell into a transgenic plant or plant cell.

The present invention also relates to methods of producing a polypeptide of the present invention comprising (a) cultivating a transgenic plant or a plant cell comprising a polynucleotide encoding the polypeptide under conditions conducive for production of the polypeptide; and (b) recovering the polypeptide.

Compositions

The present invention also relates to compositions comprising a polypeptide of the present invention. The composition may comprise a polypeptide of the present invention as the major enzymatic component, e.g., a mono-component composition. Alternatively, the composition may comprise additional enzymes, such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase. The further enzyme may also be a polypeptide having phospholipase A1, A2, B and/or D activity. The additional enzyme(s) may be produced, for example, by a microorganism belonging to the genus *Aspergillus*, e.g., *Aspergillus aculeatus, Aspergillus awamori, Aspergillus foetidus, Aspergillus fumigatus, Aspergillus japonicus, Aspergillus nidulans, Aspergillus niger*, or *Aspergillus oryzae; Fusarium*, e.g., *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium suiphureum, Fusarium toruloseum, Fusarium trichothecioides*, or *Fusarium venenatum; Humicola*, e.g., *Humicola insolens* or *Humicola lanuginosa*; or *Trichoderma*, e.g., *Trichoderma harzianum, Trichoderma koningii, Trichoderma longibrachiatum, Trichoderma reesei*, or *Trichoderma viride*.

The compositions may be prepared in accordance with methods known in the art and may be in the form of a liquid or a dry composition. For instance, the composition may be in the form of a granulate or a microgranulate. The polypeptide may be stabilized in accordance with methods known in the art.

Uses

The present invention is also directed to methods for using the polypeptides having phospholipase C activity, or compositions thereof.

The phospholipase of the invention may be applied in a process comprising treatment of a phospholipid or lysophospholipid with the phospholipase. Upon contacting with the phospholipase C the phospholipid or lysophospholipid is hydrolysed to yield diglyceride and a phosphate ester, or monoglyceride and a phosphate ester, respectively.

The phospholipase of the invention may be applied in a process comprising degumming of vegetable oil, e.g. an edible vegetable oil, in a process comprising hydrolysis of phospholipids to obtain improved phospholipid emulsifiers, in particular wherein said phospholipid is lecithin, in a process comprising hydrolysis of phospholipids in the gum fraction from water degumming to release entrapped triglyceride oil, in a process for improving the filterability of an aqueous solution or slurry of carbohydrate origin which contains phospholipid, and/or in a process for making a baked product, comprising adding the phospholipase to a dough, and baking the dough to make the baked product.

A polypeptide of the present invention may be used for degumming an aqueous carbohydrate solution or slurry to improve its filterability, particularly, a starch hydrolysate, especially a wheat starch hydrolysate which is difficult to filter and yields cloudy filtrates. The treatment may be performed using methods well known in the art. See, for example, EP 219,269, EP 808,903.

A polypeptide of the present invention may be used in a process to reduce the phospholipid content in an edible oil. See, for example, WO 2007/103005 and US 2008/0182322. Such a process is applicable to the purification of any edible oil which contains phospholipid, e.g., vegetable oil such as soybean oil, rape seed oil, and sunflower oil.

The phospholipase treatment can be carried out directly in the crude oil or after removal of slime (mucilage) e.g. by wet refining. After wet refining the oil typically will contain 50-250 ppm of phosphorus as phospholipid at the beginning of the treatment with the phospholipase, and the treatment may reduce the phosphorus value, preferably to below 11 ppm, such as to below 5-10 ppm.

The phospholipase treatment is conducted by dispersing an aqueous solution of the phospholipase, preferably as droplets with an average diameter below 10 microM. The amount of water is preferably 0.5-5% by weight in relation to the oil. An emulsifier may optionally be added. Mechanical agitation may be applied to maintain the emulsion. The phospholipase treatment can be conducted at a pH in the range of about 1.5 to about 7.0, preferably 3.5 to about 6. A suitable temperature is generally 30-70° C. (particularly 40-60° C., e.g., 55-55° C.).

The reaction time will typically be 1-12 hours (e.g., 1-6 hours, or 1-3 hours). A suitable enzyme dosage will usually be 0.1-10 mg per liter (e.g., 0.5-5 mg per liter). The phospholipase treatment may be conducted batchwise, e.g., in a tank with stirring, or it may be continuous, e.g., a series of stirred tank reactors. The phospholipase treatment may be followed by separation of an aqueous phase and an oil phase.

The separation may be performed by conventional means, e.g., centrifugation. When a liquid lipase is used the aqueous phase will contain phospholipase, and the enzyme may be re-used to improve the process economy.

A polypeptide of the present invention and other such polypeptides having activity towards one or more of the four major phospholipids phosphatidylcholine (PC), phosphatidylethanolamine (PE), phosphatidic acid (PA) and phosphatidyl inositol (PI) may be used for degumming an oil composition. Accordingly the invention provides a method for degumming an oil composition, the method comprising (a) providing an oil composition containing a quantity of phospholipids, (b) contacting said oil composition with a phospholipase C enzyme under conditions sufficient for the enzyme to react with the phospholipids to create diacylglycerol and phosphate ester, and, (c) separating the phosphate ester from the oil composition, thereby obtaining a degummed oil composition, wherein the phospholipase C enzyme has activity towards one or more of phosphatidylcholine (PC), phosphatidylethanolamine (PE), phosphatidic acid (PA) and phosphatidyl inositol (PI).

In addition to the phospholipase C of the present invention a further enzyme may be applied in the degumming process outlined above. In a preferred embodiment the further enzyme is a polypeptide having phospholipase A1, A2, B and/or D activity. A suitable polypeptide having phospholipase A1 activity may be Lecitase Ultra available from Novozymes A/S. A suitable polypeptide having phospholipase D activity may be e.g., an enzyme derived from Saccharomyces cerevisiae and having the sequence UniProt: P36126, or an enzyme derived from Dictyostelium discoideum and having the sequence UniProt: Q54Z25.

The degumming process may comprise (a) providing an oil composition containing a quantity of PC, PE, and/or PI, (b) treating said oil composition with a phospholipase D enzyme to convert PC, PE and/or PI, into PA, (c) treating said oil composition with a phospholipase C enzyme to convert PA in to diglyceride and phosphoric acid. The phospholipase D and phospholipase C may be applied together such that steps (b) and (c) occur substantially simultaneously.

Immobilization of the phospholipase on a suitable carrier may also be applied using any method known in the art incl. by entrapment in natural or synthetic matrices, such as hydrophobic polymers, ion exchanged resins, sol-gels, alginate, and carrageenan; by cross-linking methods such as in cross-linked enzyme crystals (CLEC) and cross-linked enzyme aggregates (CLEA); or by precipitation on salt crystals such as protein-coated micro-crystals (PCMC).

In certain embodiments the present invention relates to a method of producing a fatty acid ester product, wherein the carrier is a hydrophilic carrier selected from the group containing: porous in-organic particles composed of alumina, silica and silicates such as porous glas, zeolites, diatomaceous earth, bentonite, vermiculite, hydrotalcite; and porous organic particles composed of carbohydrate polymers such as agarose or cellulose. In other embodiments the present invention relates to a method of producing a fatty acid ester product, wherein the carrier is a hydrophobic polymeric carrier, e.g. polypropylen, polyethylene, acrylate. Suitable commercial carriers are e.g. LEWATIT™, ACCUREL™, PUROLITE™ and AMBERLITE™.

The present invention is further described by the following examples that should not be construed as limiting the scope of the invention.

EXAMPLES

Example 1

Phospholipase C activity assay: Reaction mixtures comprising 10 microL of a 100 mM p-nitrophenyl phosphoryl choline (p-NPPC) solution in 100 mM Borax-HCl buffer, pH 7.5 and 90 microL of the enzyme solution are mixed in a microtiter plate well at ambient temperature. The microtiter plate is then placed in a microtiter plate reader and the released p-nitrophenol is quantified by measurement of absorbance at 410 nm. Measurements are recorded during 30 min at 1 minute intervals. Calibration curves in the range 0.01-1 microL/ml p-nitrophenol are prepared by diluting a 10 micromol/ml p-nitrophenol stock solution from Sigma in Borax-HCl buffer. One unit will liberate 1.0 micromol/minute of p-NPPC at ambient temperature.

Example 2

The thermostability of the phospholipase C of the present invention (EmPLC5) was determined at pH 4.0, pH 5.5 and pH 7.0 by Differential Scanning calorimetry (DSC) using a VP-Capillary Differential Scanning calorimeter (MicroCal Inc., Piscataway, N.J., USA) at a protein concentration of approximately 0.5 mg/ml. The thermal denaturation temperature, Td (° C.), was taken as the top of denaturation peak (major endothermic peak) in thermograms (Cp vs. T) obtained after heating enzyme solutions in buffer at a constant programmed heating rate of 200 K/hr. Sample- and reference-solutions (approx. 0.2 ml) were loaded into the calorimeter (reference: buffer without enzyme) from storage conditions at 10° C. and thermally pre-equilibrated for 20 minutes at 20° C. prior to DSC scan from 20° C. to 100° C. Denaturation temperatures (Td) were determined at an accuracy of approximately +/−1° C. (Table 1).

TABLE 1

| Denaturation temperatures for EmPLC5 | | |
|---|---|---|
| pH | Buffer | Td (° C.) |
| 4.0 | Acetate | 90 |
| 5.5 | Acetate | 88 |
| 7.0 | HEPES | 83 |

Example 3

Substrate Specificity

To ensure a uniform substrate with a high concentration of all four relevant phospholipids (PC, PE, PI and PA) a test substrate is produced from soy bean oil spiked with commercial lecithin. This substrate is then incubated with enzyme and citrate buffer. Citrate is used since some degumming applications involve preconditioning the oil with citric acid. After the desired reaction time, the reaction mixture is analyzed by P-NMR. This involves an aqueous extraction step during which the phosphor species liberated by the PLC are removed from the oil phase. Hence, only lipophilic P-species are detected, including unreacted phospholipid.

The substrate is a fully refined soybean oil with added lecithin (a 2:1 ratio of the Sigma products P6636 (PI, CAS 97281-52-2) and 61755 (PC, CAS 8002-43-5)) added to a concentration of 50 mg/mL oil. This mixture will also to contain PA and PE. Disperse 250 μL into 2 mL Eppendorf tubes.

The assay is conducted at three different pH values, 4.0, 5.5 and 7.0 in 100 mM Na-citrate buffer and an enzyme concentration of 0.9 mg/mL. The enzyme amount applied is 100 mg EP/kg oil.

Before NMR analysis, samples are extracted with 100 mL 0.2 M Cs-EDTA pH 7.5 solution. Preparation of this solution: EDTA (5.85 g) is dispersed in water (approx. 50 mL). The pH is adjusted to 7.5 using 50% w/w CsOH (approx. 30 mL), which will dissolve the EDTA completely. Water is added up to 100 mL to give a concentration of 0.2 M EDTA.

Also, an internal standard solution (IS) of 2 mg/mL triphenylphosphate (TPP) in MeOH is used.

To the Eppendorf with 250 µL substrate in oil is added 25 µL diluted enzyme. The Eppendorf is incubated in thermoshaker at 50° C. for 2 h, followed by NMR analysis as described below.

To the oil sample is then added 0.500 mL IS-solution, followed by 0.5 mL $CDCl_3$ and 0.5 mL Cs-EDTA buffer. Shake for 30 s, then do centrifugation (tabletop centrifuge, 1 min, 13,400 rpm) to get phase separation. The lower phase is transferred to a NMR-tube.

P-NMR is performed with 128 scans and a delay time of 5 s. Scale reference is set according to IS signal (−17.75 ppm). Integrate all signals. Assignments (approx. ppm @ 25 C): 1.7 (PA), −0.1 (PE), −0.5 (PI), −0.8 (PC). The position of the signals can change significantly according to exact pH value, temperature, sample concentration, etc. The concentration of each species is calculated as "ppm P", i.e. mg elemental P per kg oil sample. Hence, ppm P=I/I(IS)*n(IS)*M(P)/m(oil).

The phospholipase of the invention EmPLC5 and the commercial phospholipase C Purifine were incubated with the test substrate and analysed as described above. The results are shown below.

TABLE 2

Remaining (non-hydrolyzed) phospholipids in ppm P

|  | PA | PE | PI | PC |
|---|---|---|---|---|
| Blank | 180 | 349 | 595 | 431 |
| EmPLC5, pH 4.0 | 91 | 173 | 0 | 43 |
| EmPLC5, pH 5.5 | 69 | 164 | 0 | 51 |
| EmPLC5, pH 7.0 | 0 | 201 | 0 | 69 |
| Purifine, pH 4.0 | 256 | 388 | 609 | 391 |
| Purifine, pH 5.5 | 175 | 204 | 598 | 111 |
| Purifine, pH 7.0 | 169 | 0 | 594 | 0 |

The data shows that the phospholipase C of the present invention (EmPLC5) has activity on all four phospholipids over a broad pH range. In contrast, Purifine has activity on PE and PC only at neutral pH.

Example 4

Performance in Degumming Assay

Performance/activity of the *P. emersonii* phospholipase (EmPLC5) in degumming application was determined in an assay (described below) that mimics industrial scale degumming, followed by oil phase measurement of a) diglyceride content by High-performance liquid chromatography (HPLC) coupled to Evaporative Light Scattering Detector (ELSD), and b) quantification of the individual phospholipids species: Phosphatidylcholine (PC); Phosphatidylinositol (PI); Phosphatidylethanolamine (PE); Phosphatidic acid (PA); Phosphatidylserine (PS) by HPLC-mass spectrometry (MS) and C) total phosphorous reduction by Inductively coupled plasma optical emission spectrometry (ICP-OES).

Degumming Assay

Crude soybean oil (25-75 g) was initially acid/base pretreated (or not) to facilitate conversion of insoluble phospholipids salt into more hydratable forms and ensure an environment suitable for the enzyme. Acid/base pretreatment was done by acid addition and mixing in ultrasonic bath (BRANSON 3510) for 5 min and incubation in rotator for 15 min followed by base neutralization in ultrasonic bath for 5 min. Enzyme reaction was conducted in low aqueous system (3% water total based on oil amount) in centrifuge tubes. Samples were ultrasonic treated for 5 min, followed by mixing (Stuart SB3 rotator) under incubation in heated cabinet at selected temperature. Enzyme treated oil+enzyme+water mix was then heated/centrifuged at 85° C., 15 min, 700 g (Koehler Instruments, K600X2 oil centrifuge) to separate in an oil phase and a heavy water/gum phase.

Diglyceride Measurement

The HPLC-ELSD method (using DIONEX equipment and Lichrocart Si-60, 5 µm, Lichrosphere 250-4 mm, MERCK column) is based on the principle of the AOCS Official Method Cd 11d-96 and quantifies the diglyceride content down to 0.1 wt %.

Phosphorous/Phosphorlipid Measurement

The ICP-OES quantifies the phosphorous (P) content and other metals such as Ca, Mg, Zn down to 4 ppm with an accuracy of approximately ±1 ppm P.

Example 5

The phospholipase of the invention was applied in a degumming experiment conducted over 24 hrs at various temperatures applying crude soybean oil spiked with 1% PI/PA lecithin. The treatments are shown in table 3 and the results in table 4.

TABLE 3

The treatments comprised oil, phosphoric acid solution, sodium hydroxide, water, enzyme and reaction time according to the scheme below.

| | Degumming with acid/base pretreatment | | Water degumming | |
|---|---|---|---|---|
| Sample | Blank | EmPLC5 | Blank | EmPLC5 |
| Oil amount (g) | 25 | 25 | 25 | 25 |
| Phosphoric acid 85% (ul) | 8.7 | 8.7 | 0 | 0 |
| 4M NaOH (ul) | 25.5 | 25.5 | 0 | 0 |

TABLE 4

Diglyceride formed over time while degumming with phospholipase EmPLC5 (diglyceride increase compared to blank sample).

| | Acid/base pretreated oil prior to degumming Reaction time (hours) | | | Water degummed Reaction time (hours) | | |
|---|---|---|---|---|---|---|
| Temperature (° C.) | 2 | 4 | 24 | 2 | 4 | 24 |
| 55 | 0.00 | 0.47 | 1.17 | 0.00 | 0.62 | 1.09 |
| 65 | 0.00 | 0.02 | 0.28 | 0.27 | 0.35 | 0.77 |
| 70 | 0.29 | 0.43 | 1.50 | 0.26 | 0.48 | 1.55 |
| 75 | 0.39 | 0.59 | 1.34 | 0.46 | 0.65 | 1.54 |
| 80 | 0.21 | 0.42 | 1.26 | 0.26 | 0.45 | 1.41 |

Degumming with the phospholipase C of the invention resulted in significant diglyceride formation in a broad temperature range from 55° C. to 80° C., and the EmPLC5 appears very suitable for use at elevated temperatures of 70-80° C. Good performance in water degumming as well as acid assisted degumming is observed demonstrating robustness towards varying pH conditions.

Example 6

The phospholipase C EmPLC5 was used in degumming of a crude soybean oil rich in non-hydratable phospholipids (145 ppm P non-hydratable phospholipids out of 700 ppm P total). Degumming was performed at an oil amount of 75 g, at 70° C. for 24 hrs using varying levels of acidity (0, 0.5, 1.0 and 1.5 eqv NaOH).

TABLE 5

Diglyceride formed during degumming with acid/base treatment using 0.05% phosphoric acid and varying equivalents of NaOH. Diglyceride % analysed by HPLC

| Sample | | Diglyceride % | | | |
|---|---|---|---|---|---|
| | | 0 hrs | 2 hrs | 4 hrs | 24 hrs |
| Blank 0 eqv. NaOH | 0.05% PA | 0.43 | 0.54 | 0.43 | 0.44 |
| Blank 0.5 eqv. NaOH | 0.05% PA + 0.5 eqv NaOH | 0.43 | 0.42 | 0.43 | 0.47 |
| Blank 1.0 eqv. NaOH | 0.05% PA + 1.0 eqv NaOH | 0.43 | 0.43 | 0.43 | 0.48 |
| Blank 1.5 eqv. NaOH | 0.05% PA + 1.5 eqv NaOH | 0.43 | 0.44 | 0.44 | 0.48 |
| EmPLC5 0 eqv. NaOH | 0.05% PA | 0.43 | 0.55 | 0.50 | 0.88 |
| EmPLC5 0.5 eqv. NaOH | 0.05% PA + 0.5 eqv NaOH | 0.43 | 0.54 | 0.68 | 1.24 |
| EmPLC5 1.0 eqv. NaOH | 0.05% PA + 1.0 eqv NaOH | 0.43 | 0.56 | 0.71 | 1.19 |
| EmPLC5 1.5 eqv. NaOH | 0.05% PA + 1.5 eqv NaOH | 0.43 | 0.44 | 0.46 | 0.76 |

TABLE 6

Free fatty acid and metals in degummed oil after degumming for 24 h.

| Sample | FFA wt % | Metal composition | | | |
|---|---|---|---|---|---|
| | | P | Ca | Mg | Zn |
| Blank 0 eqv. NaOH | 1.12 | 99 | 55 | 19 | 17 |
| Blank 0.5 eqv. NaOH | 1.09 | 75 | 46 | 15 | 14 |
| Blank 1.0 eqv. NaOH | 1.04 | 101 | 70 | 26 | 18 |

TABLE 6-continued

Free fatty acid and metals in degummed oil after degumming for 24 h.

| Sample | FFA wt % | Metal composition | | | |
|---|---|---|---|---|---|
| | | P | Ca | Mg | Zn |
| Blank 1.5 eqv. NaOH | 1.06 | 111 | 80 | 34 | 13 |
| EmPLC5 0 eqv. NaOH | 1.11 | 52 | 58 | 16 | 12 |
| EmPLC5 0.5 eqv. NaOH | 1.07 | 36 | 70 | 20 | 12 |
| EmPLC5 1.0 eqv. NaOH | 1.07 | 52 | 50 | 14 | 8 |
| EmPLC5 1.5 eqv. NaOH | 1.09 | 138 | 123 | 46 | 14 |

The phospholipase of the invention EmPLC5 demonstrated high and robust performance in acid assisted degumming with preference for an acidic degumming environment only partly neutralized with sodium hydroxide. At 0.05% phosphoric acid+partial neutralization with 0.5 equivalent NaOH (compared to acid dosage) significant diglyceride increase as well as phosphorous reduction was observed.

No free fatty acid increase was observed in the degumming assay which demonstrates that EmPLC5 is active on the phosphatide of the phospholipid molecule only.

Example 7

Based on the amino acid sequence in SEQ ID NO:2 a variant EmPLC5.1 comprising the substitutions K57A, C173A, K180N, I216V, V320I, D321E, T365L, I397E, Q399H, Q518K and A558S was prepared. Preliminary data showed that the stability of the variant was substantially unchanged and the phospholipase C activity was maintained.

Example 8

The wildtype phospholipase EmPLC5 and the variant EmPLC5.1 applied in degumming. The diglyceride content and total content of phosphorous after enzymatic degumming with/without acid/base pretreatment for 24 hrs, were measured. The treatments are shown in table 7 and the results in table 8.

TABLE 7

The treatments comprised oil, phosphoric acid solution, sodium hydroxide, water, enzyme and reaction time and temperature according to the scheme below.

| | Degumming with acid/base pretreatment | | | Water degumming | | |
|---|---|---|---|---|---|---|
| Sample | Blank | EmPLC5 | Variant EmPLC5 1 | Blank | EmPLC5 | Variant EmPLC5 1 |
| Oil amount (g) | 75.0 | 75.0 | 75.0 | 75.0 | 75.0 | 75.0 |
| Phosphoric acid 85% (ul) | 26 | 26 | 26 | — | — | — |
| 4M NaOH (ul) | 48 | 48 | 48 | — | — | — |

TABLE 8

Increase of diglyceride after enzyme treatment of acid/base pretreated soybean oil measured by HPLC-ELSD and content of total phosphorous measured by ICP-OES. Crude soybean oil contains 711 mg/kg of phosphorous

| Sample | Diglyceride increase (wt %) | | | Phosphorous content total (mg/kg) |
|---|---|---|---|---|
| Reaction time (hours) | 2 | 4 | 24 | — |
| EmPLC5 | 0.09 | 0.03 | 0.82 | 13 |
| Variant EmPLC5.1 | 0.09 | 0.05 | 0.39 | 19 |

In the degumming assay the phospholipase C EmPLC5 as well as the variant EmPLC5.1 convert phospholipids into diglycerides. Both enzymes work well in the acidic environment when oil is acid/base pre-treated.

TABLE 3C

Content of individual phospholipids (PC, PE, PI, PA) after enzymatic degumming for 24 hours of acid/base pretreated soy bean oil. Measured by HPLC-MS.

|  | PA mg/kg | PC mg/kg | PE mg/kg | PI mg/kg |
| --- | --- | --- | --- | --- |
| EmPLC5 | 2.3 | <2 | <2 | 1.5 |
| Variant EmPLC5.1 | 4.7 | <2 | 2.9 | 1.7 |

In acid assisted degumming conducted the phospholipase of the invention EmPLC5 and the variant EmPLC5.1 reduces all phospholipid species (PA, PI, PC, PE).

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

The invention claimed is:

1. A nucleic acid construct or expression vector comprising a polynucleotide encoding a polypeptide having phospholipase C activity, wherein the polypeptide has at least 90% sequence identity to the mature polypeptide of SEQ ID NO: 2 and the polynucleotide is operably linked to one or more control sequences that direct the production of the polypeptide in an expression host.

2. The nucleic acid construct or expression vector of claim 1, wherein the polypeptide has at least 95% sequence identity to the mature polypeptide of SEQ ID NO: 2.

3. The nucleic acid construct or expression vector of claim 1, wherein the polypeptide has at least 97% sequence identity to the mature polypeptide of SEQ ID NO: 2.

4. The nucleic acid construct or expression vector of claim 1, wherein the polypeptide comprises the sequence of amino acid residues 1-594 of SEQ ID NO: 2.

5. The nucleic acid construct or expression vector of claim 1, wherein the polypeptide is a fragment of the sequence of amino acid residues 1-594 of SEQ ID NO: 2.

6. A recombinant host cell comprising the nucleic acid construct or expression vector of claim 1.

7. A recombinant host cell comprising the nucleic acid construct or expression vector of claim 2.

8. A recombinant host cell comprising the nucleic acid construct or expression vector of claim 3.

9. A recombinant host cell comprising the nucleic acid construct or expression vector of claim 4.

10. A recombinant host cell comprising the nucleic acid construct or expression vector of claim 5.

11. A method of producing a polypeptide having phospholipase C activity, comprising:
(a) cultivating the recombinant host cell of claim 6 under conditions conducive for production of the polypeptide; and
(b) recovering the polypeptide.

12. A method of producing a polypeptide having phospholipase C activity, comprising:
(a) cultivating the recombinant host cell of claim 7 under conditions conducive for production of the polypeptide; and
(b) recovering the polypeptide.

13. A method of producing a polypeptide having phospholipase C activity, comprising:
(a) cultivating the recombinant host cell of claim 8 under conditions conducive for production of the polypeptide; and
(b) recovering the polypeptide.

14. A method of producing a polypeptide having phospholipase C activity, comprising:
(a) cultivating the recombinant host cell of claim 9 under conditions conducive for production of the polypeptide; and
(b) recovering the polypeptide.

15. A method of producing a polypeptide having phospholipase C activity, comprising:
(a) cultivating the recombinant host cell of claim 10 under conditions conducive for production of the polypeptide; and
(b) recovering the polypeptide.

* * * * *